United States Patent [19]

Englebert et al.

[11] Patent Number: 4,741,941

[45] Date of Patent: May 3, 1988

[54] NONWOVEN WEB WITH PROJECTIONS

[75] Inventors: Stephen M. Englebert, Woodstock, Ga.; Ann L. Wagner, Hortonville, Wis.; Gregory S. Hafer, Atlanta, Ga.; Nanette J. Logsdon, Appleton, Wis.

[73] Assignee: Kimberly-Clark Corporation, Neenah, Wis.

[21] Appl. No.: 794,915

[22] Filed: Nov. 4, 1985

[51] Int. Cl.[4] ......................... A61F 13/16; B32B 3/10; D04H 1/74; D04H 5/08

[52] U.S. Cl. .................... 428/71; 15/209 R; 15/209 B; 15/215; 15/217; 15/223; 19/296; 19/301; 19/302; 128/132 R; 128/156; 156/176; 156/178; 156/181; 156/252; 156/270; 156/279; 428/76; 428/112; 428/113; 428/131; 428/135; 428/138; 428/141; 428/160; 428/171; 428/172; 428/179; 428/180; 428/283; 428/286; 428/287; 428/319.7; 428/903; 428/913; 604/367; 604/376; 604/380; 604/382; 604/384; 604/385 R

[58] Field of Search ............... 428/76, 119, 131, 135, 428/138, 179, 180, 71, 112, 113, 132, 141, 283, 286, 287, 319.7, 160, 171, 172; 15/209 R, 209 B, 215, 217, 223; 19/296, 301, 302; 156/176, 178, 181, 252, 270, 279; 604/367, 376, 380, 382, 384, 385 R

[56] References Cited

U.S. PATENT DOCUMENTS

| Re. 31,345 | 7/1983 | Schwartzkopft | 119/28 |
|---|---|---|---|
| Re. 31,599 | 6/1984 | Rasen et al. | 156/167 |
| 263,531 | 8/1882 | Kacer | 428/132 |
| 3,034,180 | 5/1962 | Greiner et al. | 19/155 |
| 3,054,148 | 9/1962 | Zimmerli | 18/56 |
| 3,110,609 | 11/1963 | Bletzinger | 117/25 |
| 3,126,978 | 3/1964 | Bergstrom | 428/131 |
| 3,218,381 | 11/1965 | Such et al. | 264/103 |
| 3,240,657 | 3/1966 | Hynek | 161/109 |
| 3,285,245 | 11/1966 | Eldredge et al. | 128/156 |
| 3,336,182 | 7/1967 | Bassett et al. | 428/132 |
| 3,345,243 | 10/1967 | Kalwaites | 428/131 |
| 3,414,459 | 12/1968 | Wells | 428/340 |
| 3,419,457 | 12/1968 | Bleasdale | 428/131 |

(List continued on next page.)

FOREIGN PATENT DOCUMENTS

| 508206 | of 1955 | Italy | 428/131 |
|---|---|---|---|
| 1089414 | of 1967 | United Kingdom | 156/167 |
| 1331817 | of 1973 | United Kingdom | |

OTHER PUBLICATIONS

Dec. 83, *Plastic World,* Miller, "Processing Aids Boost Linear Low Extrusion Rates", pp. 52–53.

Apr. 1973, *Tappi,* 56, 4, pp. 74–77, Buntin et al., "Melt Blowing-A One-Step We Process for New Nonwoven Products".

*Primary Examiner*—James C. Cannon
*Attorney, Agent, or Firm*—William D. Herrick

[57] ABSTRACT

Nonwoven web and method of making including interbonded thermoplastic fibers in an array of hollow projections extending outwardly from at least one surface of said web. The projections are separated by land areas of interbonded fibers, and the fiber orientation is greater in the projections than in the land areas. Either the projections or the land areas may be perforated as desired for controlled porosity and fluid flow properties. The nonwoven webs of the invention may be made by a number of processes but, preferably, are made by forming directly on a surface with corresponding projections with or without apertures and a vacuum assist or by forming on an apertured surface with a pressure differential sufficient to draw the fibers through the apertures forming the projections. The disclosure includes such webs with added fiber layers and as components of a wide variety of products including personal care items such as liners for sanitary napkins, household products such as cleaning materials and wipers, in the service product area such as towels, washcloths and bathmats, in the marine and automotive area as scrubbing and protective applicators, and in the hospital and veterinary areas as wipes and dispensing cloths. The method and apparatus disclosed may be varied as to steps and configuration to impart desired web constructions and properties, and preferred embodiments are disclosed.

71 Claims, 12 Drawing Sheets

U.S. PATENT DOCUMENTS

| | | | |
|---|---|---|---|
| 3,441,468 | 4/1969 | Siggel et al. | 428/221 |
| 3,502,763 | 3/1970 | Hartmann | 264/210.2 |
| 3,509,009 | 4/1970 | Hartmann | 156/181 |
| 3,542,635 | 11/1970 | Parker | 428/131 |
| 3,565,729 | 2/1971 | Hartmann | 156/441 |
| 3,616,159 | 10/1971 | Kamp | 428/180 |
| 3,663,348 | 5/1972 | Tiloia et al. | 428/74 |
| 3,673,295 | 6/1972 | Winchklhofer et al. | 428/296 |
| 3,772,133 | 11/1973 | Schmitt | 428/137 |
| 3,814,208 | 6/1974 | Morresi et al. | 428/132 |
| 3,855,046 | 12/1974 | Hansen et al. | 428/288 |
| 3,857,657 | 12/1974 | Teed | 264/517 |
| 3,934,588 | 1/1976 | Mesek et al. | 128/290 W |
| 3,949,127 | 4/1976 | Ostermeier et al. | 428/137 |
| 3,989,867 | 11/1976 | Sisson | 428/132 |
| 3,994,771 | 11/1976 | Morgan et al. | 428/180 |
| 4,005,957 | 2/1977 | Savich | 264/517 |
| 4,013,816 | 3/1977 | Sabee et al. | 428/288 |
| 4,041,951 | 8/1977 | Sanford | 128/287 |
| 4,042,740 | 8/1977 | Krueger | 428/138 |
| 4,103,058 | 7/1978 | Humlicek | 428/171 |
| 4,129,097 | 12/1978 | Schwartzkopff | 428/288 |
| 4,177,312 | 12/1979 | Rasen et al. | 428/284 |
| 4,212,692 | 7/1980 | Rasen et al. | 156/167 |
| 4,219,376 | 8/1980 | Roman | 428/132 |
| 4,252,590 | 2/1981 | Rasen et al. | 156/167 |
| 4,323,069 | 4/1982 | Ahr et al. | 128/287 |
| 4,333,979 | 6/1982 | Sciaroffa et al. | 428/180 |
| 4,341,217 | 7/1982 | Ferguson et al. | 128/290 W |
| 4,342,807 | 8/1982 | Rasen et al. | 428/180 |
| 4,392,862 | 7/1983 | Marsan et al. | 604/366 |
| 4,397,644 | 8/1983 | Matthews et al. | 604/378 |
| 4,463,045 | 7/1984 | Ahr et al. | 428/131 |
| 4,469,734 | 9/1984 | Minto et al. | 428/134 |
| 4,519,798 | 5/1985 | Dinius | 604/358 |
| 4,614,679 | 9/1986 | Farrington et al. | 428/158 |

SURFACE MICROPORES

SURFACE MICROPORES

NONWOVEN WEB WITH PROJECTIONS

BACKGROUND OF THE INVENTION

1. Field of the Invention

The present invention is directed to nonwoven fabrics useful for a wide variety of applications. Such nonwovens in the form of lightweight, soft porous webs are used as cover liners for personal care products such as sanitary napkins and disposable diapers, for example. Other embodiments of nonwovens having engineered capillary structures are useful, for example, as intermediate transfer layers for such personal care products acting to distribute fluids and minimize leakage. Still others, frequently in heavier basis weights, are highly absorbent and serve as the absorbent medium for personal care products. In addition to nonwovens for personal care applications the field of the invention embraces nonwovens for many other uses, for example in the household as cleaning materials and wipers, in the service product area as towels, bathmats and the like, in the automative and marine areas for scrubbing, wiping, protective and other uses and in the hospital and veterinary areas as wipes and applicators. The field includes nonwoven fabrics broadly for these and many other uses which will be apparent in light of the description below, and preferred embodiments of will be set forth hereinafter in detail. Moreover, the field embraces methods and apparatus for manufacturing such nonwovens resulting in engineered, three-dimensionally structured webs.

2. Description of the Prior Art

The manufacture of nonwoven fabrics is a highly developed art. In general, nonwoven webs and their manufacture involve forming filaments or fibers and depositing them on a carrier in such manner so as to cause the filaments or fibers to overlap or entangle as a mat of a desired basis weight. The bonding of such a mat may be achieved simply by entanglement or by other means such as adhesive, application of heat and/or pressure to thermally responsive fibers, or, in some cases, by pressure alone. While many variations within this general description are known, two commonly used processes are defined as spunbonding and meltblowing. Spunbonded nonwoven structures are defined in numerous patents including, for example, U.S. Pat. No. 3,565,729 to Hartmann dated Feb. 23, 1971, U.S. Pat. No. 4,405,297 to Appel and Morman dated Sept. 20, 1983, and U.S. Pat. No. 3,692,618 to Dorschner, Carduck, and Storkebaum dated Sept. 19, 1972. Discussion of the meltblowing process may also be found in a wide variety of sources including, for example, an article entitled, "Superfine Thermoplastic Fibers" by Wendt in *Industrial and Engineering Chemistry,* Volume 48, No. 8, (1956) pages 1342–1346 as well as U.S. Pat. No. 3,978,185 to Buntin, Keller and Harding dated Aug. 31, 1976, U.S. Pat. No. 3,795,571 to Prentice dated Mar. 5, 1974, and U.S. Pat. No. 3,811,957 to Buntin dated May 21, 1974. Spunbonded webs and meltblown webs are widely used for many applications, including personal care products as described, for example, in U.S. Pat. No. 4,397,644 to Matthews, Allison, Woon, Stevens, and Bornslaeger, dated Aug. 9, 1983 or U.S. Pat. No. 4,372,312 to Fendler and Bernardin dated Feb. 8, 1983. Other nonwoven manufacturing processes include carding, wetlaying and needing, but the invention will be described with particular reference to meltblown and spunbonded webs which represent preferred embodiments.

In addition to processes for making nonwovens, in general, it is known to form nonwoven fabrics, broadly, into so-called "three-dimensional" configurations that result in a web having a base plane but wherein fibers project out of the base plane in one, several or many different forms. For example, U.S. Pat. No. 4,103,058 to Humlicek dated July 25, 1978 describes a pillowed web of meltblown microfibers where a pattern of pillowed low density regions is separated by high density areas formed by collecting on a perforated screen. U.S. Pat. No. 4,041,951 to Sanford dated Aug. 16, 1977 describes a nonwoven web containing a multiplicity of depressed areas providing wet resilience in a diaper top sheet that tends to isolate the wearer's skin from moisture contained in the absorbent layer. U.S. Pat. No. 3,240,657 to Hynek dated Mar. 15, 1966 describes an apertured web wherein the perforations are formed between relative low density web areas. Various forming techniques for making matting structures are described in prior art patents such as U.S. Pat. No. RE31,599 to Rasen, Vollbrecht and Schenesse dated June 12, 1984 which discusses forming on a variety of surfaces having projections of different types and U.S. Pat. No. 4,488,928 to Kon and Schmidt dated Dec. 18, 1984 which discusses the use of vacuum drawing fibers onto various wire or belt forming surfaces.

Notwithstanding the intense investigation into the subject, there remains desired a nonwoven fabric that can be produced with widely varying, but carefully controlled, properties such as permeability, bulk, absorbency, liquid transmission, flexibility or stiffness, and density.

SUMMARY OF THE INVENTION

In accordance with the present invention there is provided an improved nonwoven fabric having controlled porosity, liquid flow, absorbency and other physical properties that is useful for the above-described applications in personal care, household, automotive and health care products, and for many other purposes such as scrubbers, bathmats, washcloths, and the like. In accordance with the invention, the nonwoven fabric comprises an array of interbonded thermoplastic fibers. The fabric of the invention is further defined by a pattern of hollow projections extending out of the base plane of the web wherein the fibers or filaments are more aligned than in the land areas between the projections. The projections in accordance with the invention average in the range generally of from about one per square centimeter to about eighty per square centimeter, and have an average height measured from the base plane to the most extended fibers within the range generally of from about 0.3 mm to 25 mm. The web of the invention is further characterized by an average bulk density in the range generally of from about 0.001 g/cc to about 0.11 g/cc. The fiber diameter in accordance with the invention may vary generally from about one micron to about 100 microns. Other important parameters include the variation in fiber alignment between the web land and projection areas. In accordance with the invention the projections include fibers or filaments with an average alignment of at least 5° greater than the average alignment of the fibers or filaments in the land areas. Also, the webs of the invention may be characterized by a volume ratio of volume of the porjections to volume contained between the projections, in both cases measured between planes at the base and tops of the projections, in the range of from about 1 to 250. In accordance with the invention the fibers or filaments forming the web may be produced by a wide variety of means including the spunbonded and meltblowing processes known to the art and mentioned above. The hollow projections in the web can also be formed in different ways. Preferably, however, the desired fiber alignment and bulk denisty are obtained in a manner that provides a pressure differential to the fibers or filaments such as by forming onto a surface having projections with a vacuum assist or by forming on a porous surface with a vacuum applied to the side of the surface opposite that receiving the filaments. In an alternative embodiment the nonwoven fabric of the present invention may contain apertures caused by forcing the fibers over the projections in the forming surface or by forcing the fibers through the forming surface by a pressure differential. Alternatively, various post-treatments such as shaving, for example, may be used. The present invention also includes preferred product embodiments incorporating the nonwoven fabric with hollow projections with or without apertures such as, for example, personal care products such as sanitary napkins, diapers, and incontinence garments, scrubbing devices, bathmats, washcloths, and others.

DESCRIPTION OF THE PREFERRED EMBODIMENTS

Figure 1:
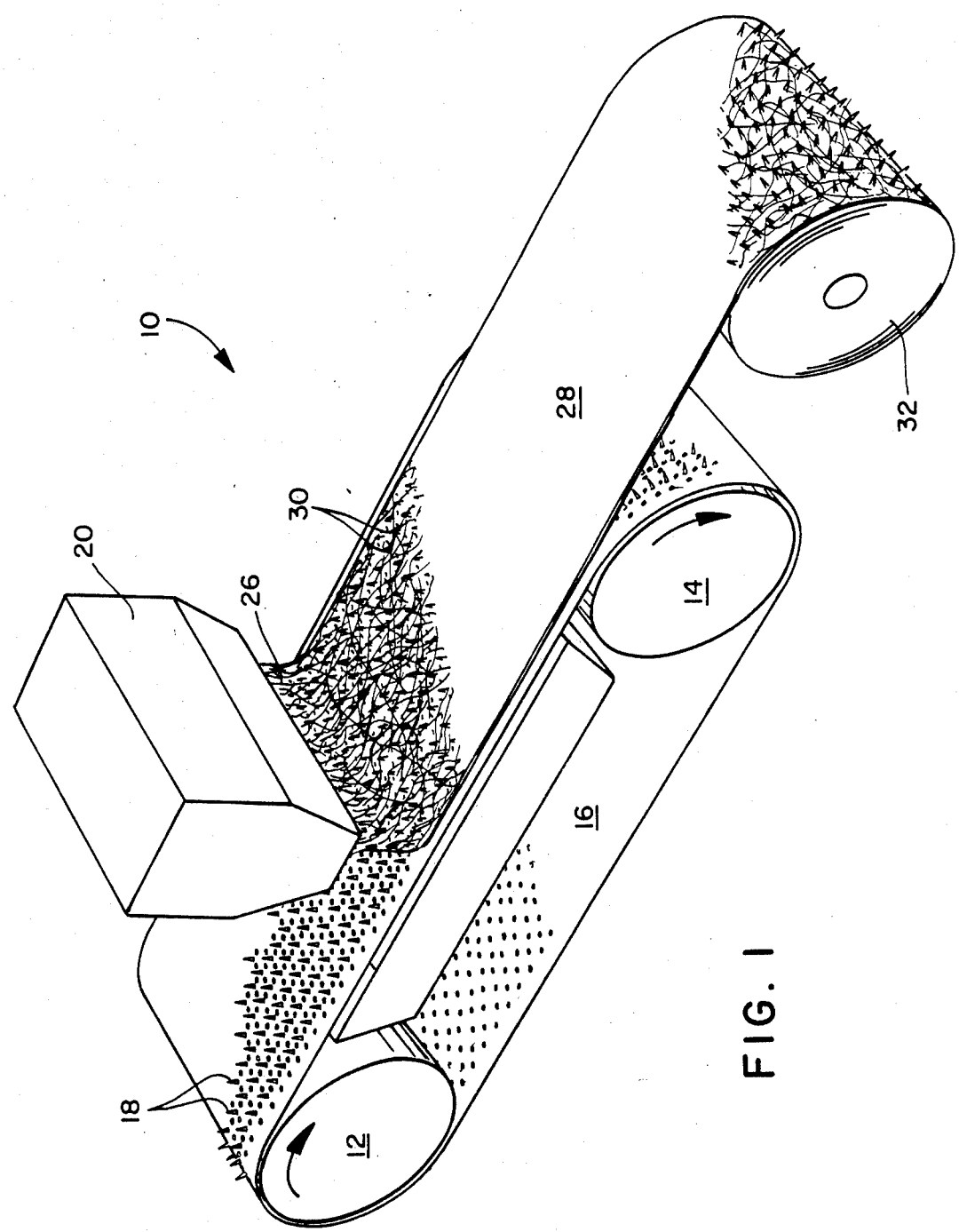
FIG. 1 is a schematic illustration of one method in accordance with the invention for forming nonwoven webs with projections using a surface having projections and apertures.

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

Certain terms as used herein will be defined to facilitate an understanding of the invention. The term "base plane" is used herein to described the plane along the surface opposite the projections or, for those embodiments with projections on both surfaces, taken along a central line parallel to the flat web ignoring the presence of any projections. The term "bulk density" refers to the density of the web using as its thickness the distance between the surface of the web away from the projections and the average height of the projections. In the case of a web having projections from both surfaces, the thickness will be the sum of the average projection height of the projections from the center of the base plane. The term "web density" is used herein to refer to the density taken in the land areas between the projections. The term "fiber alignment" is used herein to refer to the tendency of fiber or filaments in a plane to be oriented in parallel directions. It is expressed as degrees and measured using Cambridge 600 SCM photos and a Cambridge Instruments Quantimet 900 image analyzer. The device was set up to measure aperture orientation between the fibers or filaments as an indicator of fiber or filament orientation. Criteria used for apertures were: 32 feret system (implying a precision of 5.625°) apertures must be larger than 10 micrometers; apertures must be elongated with a shape factor $\pi L^2/4A < 2.0$; and acceptable angles between 0° and 100° with acceptable Sine $(\theta)$ values between 0 and 1.1 (to avoid sorting errors).

Since it is the structure of the web of the present invention which is largely responsible for the improvements obtained, the raw materials used may be selected from a wide variety. For example, and without limiting the generality of the foregoing, thermoplastic polymers such as polyolefins including polyethylene, polypropylene as well as polystyrene may be used as may be polyesters including polyethylene terephthalate, and polyamides including nylons. Also useful are other thermoplastic polymers such as those which are elastomeric including elastomeric polyurethanes and block copolymers. Compatible blends of any of the foregoing may also be used. In addition, as will be explained in greater detail later, additives such as wax, fillers, and the like may be incorporated in amounts consistent with the fiber forming process used to achieve desired results. Other fiber or filament forming materials will suggest themselves to those skilled in the art such as glass, for example. The fibers may also be formed from solution, and examples include viscose. It is only essential that the composition be capable of spinning into filaments or fibers of some form that can be deposited onto a forming surface of the invention and thermally formed or interbonded in a manner dependent upon the forming surface.

Since most of these polymers are hydrophobic, if a wettable surface is desired, known compatible surfactants may be added to the polymer as is well known to those skilled in this art. Such surfactants include, by way of example and not limitation, anionic and nonionic surfactants such as sodium dioctyl sulfosuccinate (Aerosol OT available from American Cyanamide) and alkyl phenoxy ethanol (Triton X-100 available from Rhom & Haas). The amount of surfactant additive will depend on the desired end use as will also be apparent to those skilled in this art. Other additives such as pigments, fillers, stabilizers, and the like may also be incorporated. Further discussion of the use of such additives may be had by reference to U.S. Pat. No. 4,374,888 to Bornslaeger dated Feb. 22, 1983, for example, and U.S. Pat. No. 4,070,218 to Weber dated Jan. 24, 1978 for example.

The basis weight for nonwoven fabrics produced in accordance with the invention will vary widely depending upon the intended use. For example, very lightweight webs having a basis weight in the range of from about 10 grams per square meter to 50 grams per square meter or even lighter in some cases are useful as liners for disposable diapers or for covers, liners or transfer layers in other personal care products such as sanitary napkins. The transfer layer in such a product is positioned between the absorbent layer and the liner and serves to distribute fluid passing through the liner in a manner to achieve maximum utilization of the absorbent medium. Somewhat heavier basis weights will serve for applications such as washcloths, towels, and the like, which generally, will have a basis weight in the range of from about 20 grams per square meter to about 70 grams per square meter. Still heavier products in the basis weight range of from about 70 grams per square meter to about 300 grams per square meter or even higher can be engineered to be stiffer and find uses such as a scrubber for auto windshields, for example, or for household uses. For other applications such as, for example, bathmats, it may be useful to laminate a nonwoven fabric having hollow projections produced in accordance with the present invention with an absorbent bottom layer to provide desired absorption and rigidity to the product. Examples of other products or combinations requiring similar or different nonwoven basis weights will be apparent to those skilled in the art, and some will be discussed in detail with reference to the drawings.

The number of projections for the nonwoven fabrics produced in accordance with the invention will be within the range of from about one to about eighty per square centimeter and, for many applications, will preferably be within the range of from about five to about fifty per square centimeter. The shape of the individual projections will vary depending upon how they are formed, but it is a characteristics of the present invention that the projections will be hollow and have a height in the range of from about 0.3 millimeter to about 25 millimeters preferably within the range of from about 0.5 millimeter to about 10 millimeters to provide desired properties. For example, if the projections have a greater height, they may slow fluid transfer or tend to break undesirably or fold upon themselves, in either case reducing the effectiveness of the web for many intended applications. On the other hand, hollow projections with smaller height will not achieve the desired separation from absorbent or other layers placed in contact with the projections necessary to produce improved stain hiding and resistance to flowback especially useful for sanitary personal care products.

It is also a characteristic of the present invention that the fibers or filaments in the projection areas are oriented in a parallel direction to a higher degree than those fibers or filaments in the land areas. This results from the pressure differential applied to the fibers either as the fibers or filaments are pulled over the projections on the forming surface or drawn through apertures in the forming surface. The result, in either case, is that the alignment will be at least 5° greater in the projections than in the land areas. As will be apparent from the test description above, a random web will have an angle reading of 45° while increased angles indicate greater fiber or filament alignment. While it is not desired to limit the invention to a particular theory, improvements in flow through the webs of the invention are believed attributable at least in part to this increased alignment. Capillaries within and between the fibers or filaments are favored and facilitate fluid transport.

To achieve the benefits described, the hollow projections will in many cases preferably be arranged such that they form or may be projected to form cones. While the term "cone" has been used, as will be appreciated by those skilled in this art, the actual shape of a give projection may vary, but, the average projection will in such cases most closely resemble a cone in shape or extension. The hollow core of the projections will, in general, be determined by the manner in which the projections are formed. For example, if the projections are formed by depositing fibers onto a surface with pins, the core will assume the general contour of the pins. On the other hand, if the projections are formed by a pressure differential across a foraminous carrier, the hollow core will have a configuration determined by the opening in the carrier. The term "hollow" as used herein does not completely exclude the presence of fibers or filaments in the core areas of the projections. On the contrary, as will be apparent to those skilled in this art, the forming steps described may well leave fibers in the core areas due to variabilities in air flow, fiber properties or other parameters. The term "hollow" as used herein, therefore, means that the core or centerline taken through a given projection will define a low density path substantially free from fibers or filaments when compared with the land areas or projection walls. While the core may vary widely in shape and size, for some preferred applications in personal care products it will have a volume expressed as a ratio of the projection, including the core, in the range of between about 0.25 to about 0.75, preferably about 0.3 to about 0.6. On the other hand, preferred embodiments will have a volume ratio of the volume of the projections to volume contained between the projections, measured between planes at the base and tops of projections, in the range of from about 1 to 250.

The fibers or filaments used to produce the nonwoven fabrics of the present invention may vary widely in shape, diameter, cross-section, and length. For example, continuous spunbond filaments may be used as well as meltblown continuous or discontinuous microfibers which frequently have a lower average diameter. Furthermore, additives to the web such as superabsorbent powders, liquids, or natural fibers such as wood pulp may also be incorporated at various loading levels depending upon desired end use properties.

In one particularly preferred embodiment pore size distribution within the nonwoven fabric of the invention is further controlled through addition of a hydrocarbon processing aid to the polymer being spun into fibers or filaments. Such hydrocarbon processing aids include those compositions that, in general, act as lubricants improving polymer flow properties such as melt stiffness. Examples include paraffin waxes, synthetic waxes, oxidized and unoxidized waxes. For example, when the polymer is polyethylene, wax may be added to the polymer in an amount of up to about 50 percent by weight, preferably in the range of from about 5 to 15 percent prior to spinning. The resulting web will then have finer fibers resulting in an improved hand and a narrower pore size distribution including lesser amounts of large pores as will be discussed further with reference to FIGS. 31 and 32 below. Examples of hydrocarbon processing aids that may be used include paraffinic waxes such as Ross Wax 165 from Frank B. Ross, Jr. Co. A similar controlled pore size distribution may be obtained by calendering between the projections as will be discussed in detail with reference to FIG. 15. For for many applications it is also important to have larger apertures as well as the fine pore structure already defined. Such apertures may be located in some cases in the land areas between the hollow projections or may be in some or all of the projections, themselves, either open as formed or by removing the closed portion of the projections after formation. Ways for achieving such apertures will be described below in greater detail particularly with reference to FIGS. 15, 17 and 19–21.

Turning to FIG. 1, one method for producing the nonwoven fabrics having hollow projections in accordance with the invention will be described. As shown, forming apparatus 10 includes forming surface 16 which is an endless belt disposed around support rolls 12, 14, either or both of which may be driven by means not shown such as motors, etc. Belt 16 includes pins 18 extending outward from the belt. These pins will be selected as to size and frequency so as to produce the web having the desired array and configuration of projections suitable for the intended purpose. The shape of the projections will vary according to the desired shape of the projections in the web. In this FIG. 1 a fiber forming process is schematically illustrated wherein fiber forming device 20 such as a meltblowing die, spunbonding die or spray nozzle extrudes molten filaments 26. The resulting fibers 26 are collected on the forming surface 16 as web 28 having corresponding hollow projections 30. Web 28 may be directed for further processing or, as shown, wound into roll 32.

Figure 2:
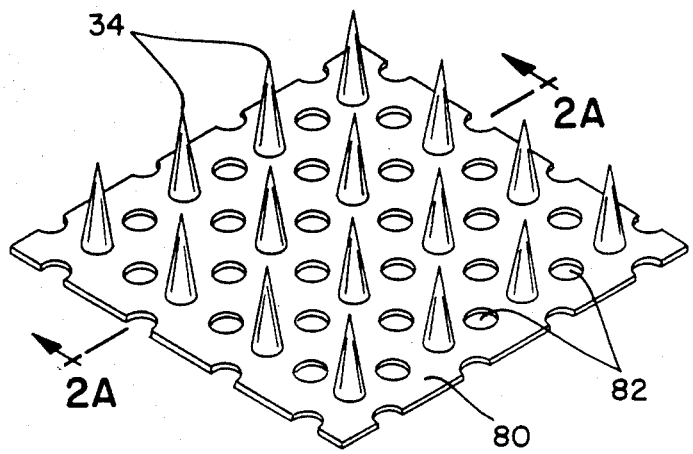
FIGS. 2 through 4 illustrate in greater detail forming surfaces with projections useful in the process of FIG. 1.
Figure 2A:
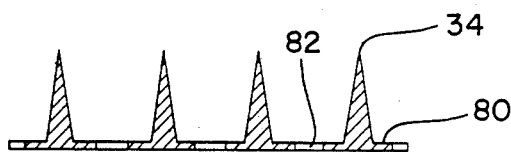
FIGS. 2A, 3A, and 4A show cross-sections taken along lines 2A—2A, 3A—3A, and 4A—4A of the respective figures.

FIG. 2 illustrates in greater detail and in perspective view one forming surface which can be used as belt 16 in FIG. 1. As shown, the surface in this case is a flat metal sheet 80 having cone-shaped pins 34 which are disposed outwardly from the surface. In this embodiment sheet 80 also contains perforations 82 which may be used for applying vacuum to increase the pressure differential applied to the filaments 26 (FIG. 1). FIG. 2A shows the forming surface of FIG. 2 in cross-section taken along lines 2A—2A. Although shown as a flat sheet, the surface may be a portion of a belt, wire or roll as will be appreciated by those skilled in this art.

Figure 3:
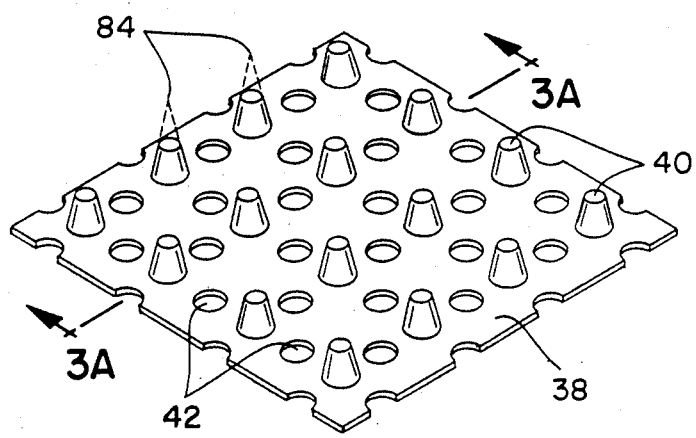
Figure 3A:
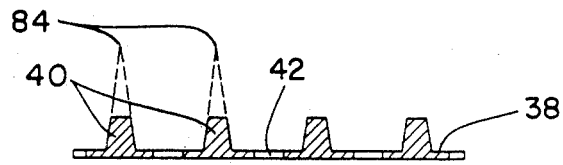

FIG. 3 is a view of an alternative forming surface 38 which, in this case, has pins 40 in the shape of truncated cones extending outwardly and apertures 42 which may be open to vacuum applied to the surface of sheet 38 opposite that to which filaments 26 (FIG. 1) are applied. FIG. 3A is a cross-section of the surface of FIG. 3 taken along lines 3A—3A. As shown in greater detail, the pins 40 in this case have a configuration the extension of which forms a cone 84.

Figure 4:
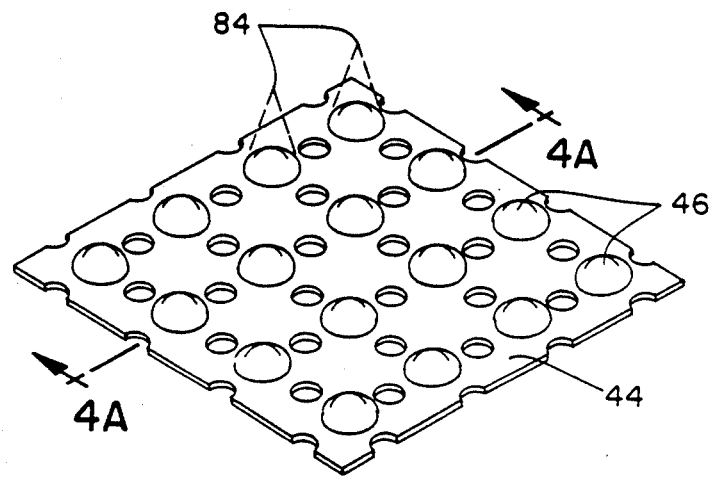
Figure 4A:

FIGS. 4 and 4A are views like FIGS. 2 and 2A illustrating yet other forming surfaces 44 having projections 46 of a domed configuration.

Figure 5:
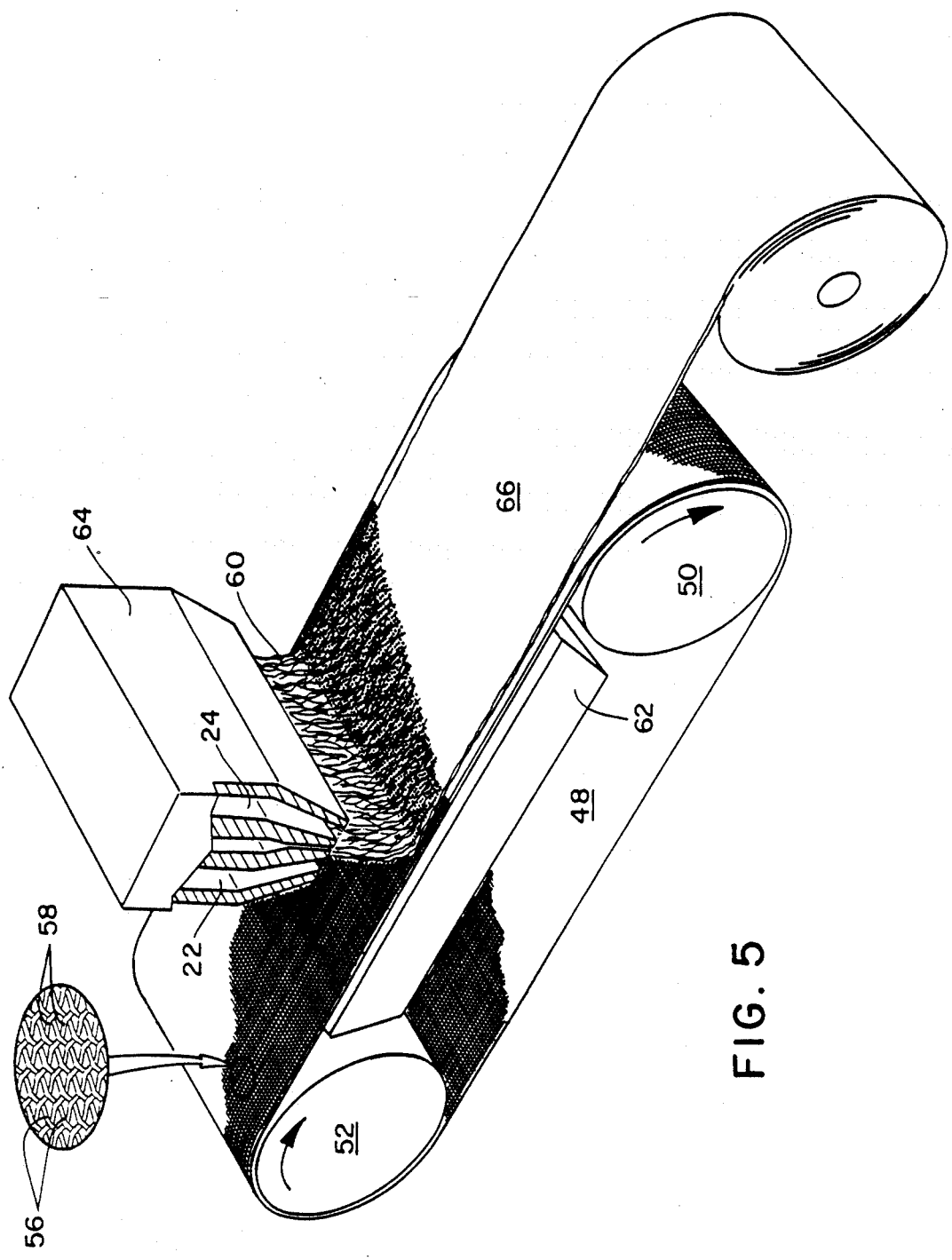
FIG. 5 illustrates an alternative vacuum forming process useful for forming nonwoven fabrics having projections in accordance with the present invention.

FIG. 5 is a schematic perspective view of an alternative forming process. As shown, a belt or wire 48 of machine direction filaments 58 and cross-machine direction filaments 56 is carried about support rolls 50, 52, either or both of which may be driven by motor means (not shown). Filaments 60 are formed, for example, by melt-blowing die 64 and contacted by air in conduits 22, 24 as in the process described in U.S. Pat. No. 3,978,185 dated Aug. 31, 1976 to Buntin, Keller, and Harding, which is incorporated herein by reference. Such filaments are ejected from die 64 and are collected on the wire 48. Suction box 62 applies a vacuum to the randomly entangled filaments which results in a pressure differential forming pockets that produce hollow projections from the undersurface of the web. The resulting web 66 with projections may then be directed for further processing.

Figure 6:
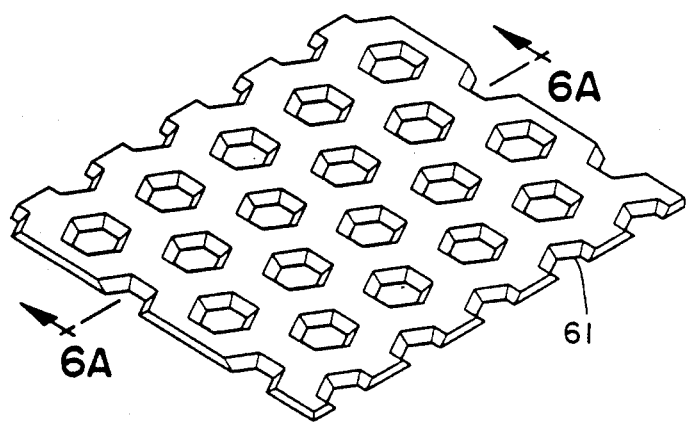
FIGS. 6 through 8 illustrate forming surfaces for the vacuum forming process.
Figure 6A:
FIGS. 6A, 7A and 8A show cross-sections taken along lines 6A—6A, 7A—7A and 8A—8A in the respective figures.

FIG. 6 illustrates an alternative belt configuration useful in the apparatus illustrated in FIG. 5, and FIG. 6A shows the belt of FIG. 6 in cross-section taken along lines 6A—6A. Such a belt would produce generally hexagonal projections.

Figure 7:
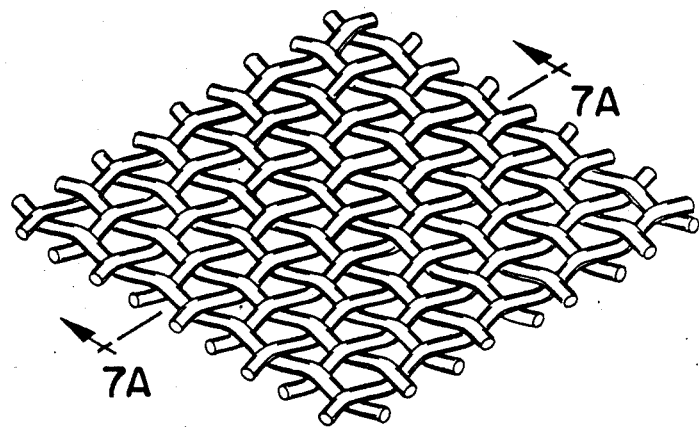
Figure 7A:

FIG. 7 illustrates an alternative wire configuration, and FIG. 7A shows the wire of FIG. 7 taken in cross-section along lines 7A—7A.

Figure 8:
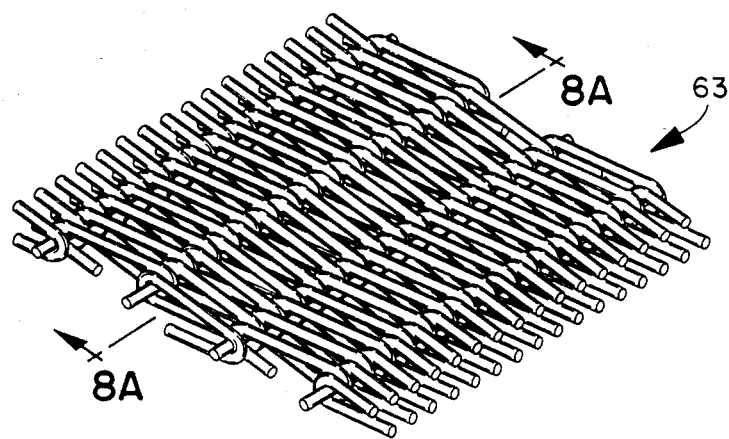
Figure 8A:

FIG. 8 illustrates a third alternative wire configuration with FIG. 8A showing the wire in cross-section taken along line 8A—8A.

Figure 9:
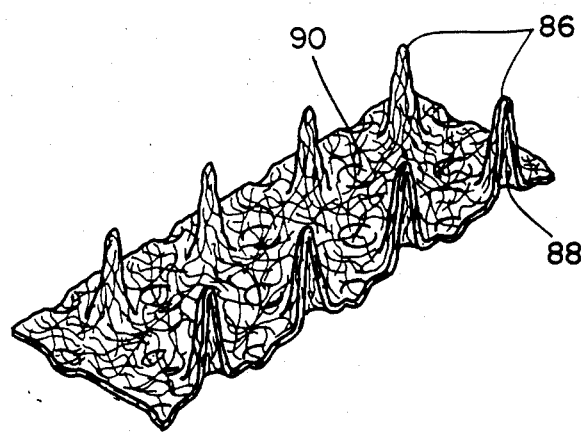
FIGS. 9 through 14 schematically illustrate webs formed on the forming surfaces of FIGS. 2 through 4 and 6 through 8 using the process of FIG. 1 for FIGS. 9 through 11 and the process of FIG. 5 for FIGS. 12 through 14.
Figure 10:
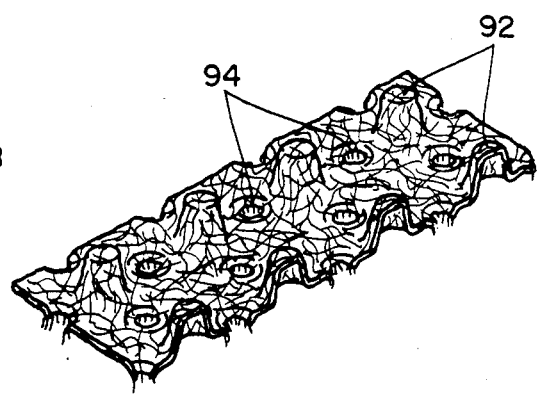
Figure 11:
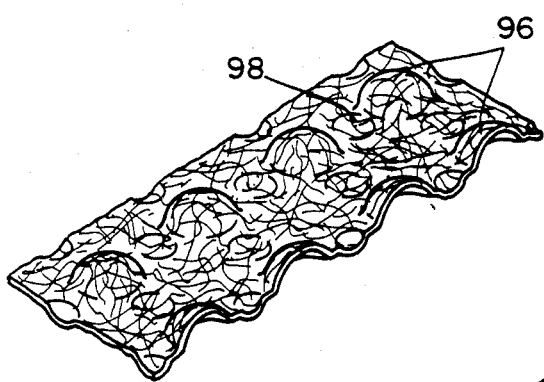

FIGS. 9 through 11 illustrate schematically webs formed on the surfaces illustrated in FIGS. 2 through 4. In FIG. 9, hollow projections 86 are cone-shaped, in general, with hollow cores 88. Each projection 86 corresponds to a projection 34 (FIG. 2). The projections 86 are formed under conditions such that they retain their shape after removal from the forming surface. Also in this case depressions 90 are formed corresponding to openings 82 (FIG. 2). In cases where a lower basis weight web is formed or where higher vacuum is applied to the web, these depressions 90 may actually result in apertures in the land areas of the web. The web of FIG. 10 has hollow projections 92 in similar manner relating to pins 40 (FIG. 3). Just as an extension of pins 40 (FIG. 3) forms cones 84 (FIG. 3), an extension of projections 92 also generally forms cone-shaped structures. In this case the forming conditions have resulted in apertures 94 in the land areas as a result of higher pressure differentials caused by increased vacuum. FIG.

11 similarly illustrates a web formed on the surface of FIG. 4. In this case hollow projections 96 are rounded but still by extension form cone-shaped structures. As in the case of FIG. 9, the forming conditions are such as to produce depressions 98.

Figure 12:
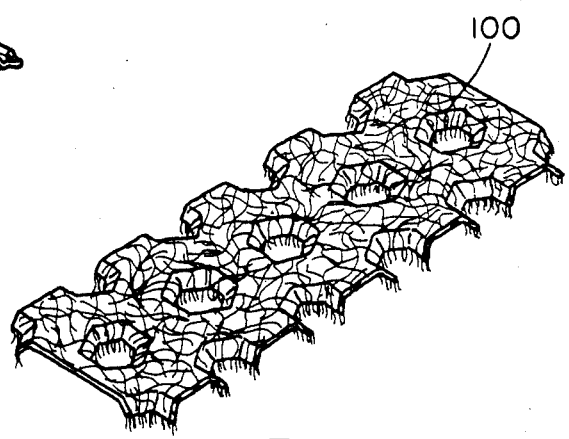
Figure 13:
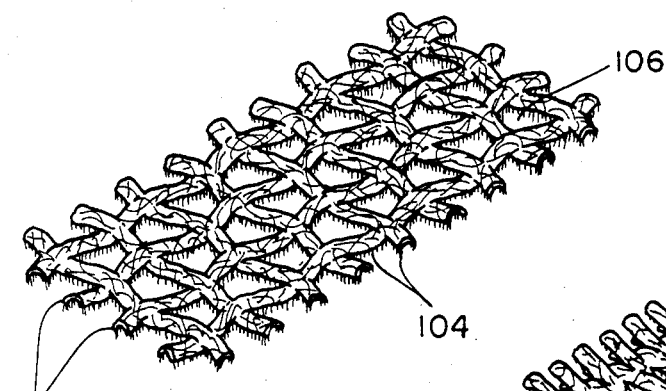
Figure 14:
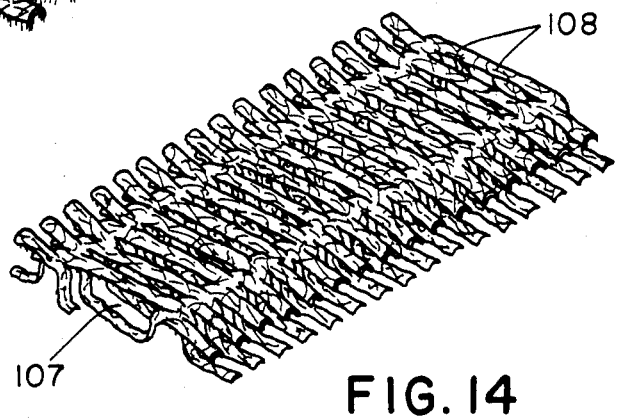

FIGS. 12 through 14 illustrate in schematic form webs formed on forming surfaces of FIGS. 6 through 8. The web of FIG. 12 includes hollow projections 100 which are hexagonally shaped but, in general, may be extended to form cone-like structures corresponding to the apertures 61 (FIG. 6). These projections are open, forming apertures as a result of the pressure differential applied to the forming surface. The web of FIG. 13 shows less well defined projections 102 formed by filament-like forms 104 surrounding apertures 106. In like manner the web of FIG. 14 contains hollow projections 107 formed by filament-like structures 108 as a result of vacuum applied to wire 63 (FIG. 8).

Figure 15:
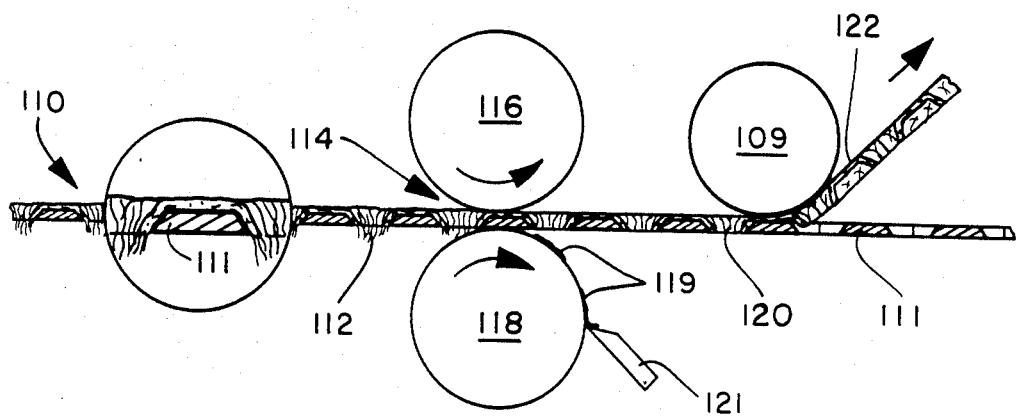
FIG. 15 illustrates calendering means for controlling web porosity in accordance with the invention, and FIG. 16 schematically illustrates web formed in this manner.

FIG. 15 illustrates schematically one means for controlling the porosity of the web of the present invention particularly in the land areas. As shown, web 110 having projections 112 travels with forming surface 111 in the direction indicated through nip 114 between calender rolls 116, 118. These rolls apply pressure to the combined web and forming surface which produces compaction primarily in land areas 122. This step also serves to modify apertures 120 by removing loose fibers, particularly if roll 118 is heated at or near the polymer melting point. Such loose fibers adhere to roll 118 at areas 119, for example, and are removed by blade 121. In a preferred embodiment both rolls may be heated with bottom roll 118 at a higher temperature to cause the polymer 119 to preferentially adhere. If desired, one of these rolls may also serve as the forming surface having a surface as in FIG. 6, for example, with vacuum applied and web forming at or near the nip 114. In such a case the web, after calendering at pressures sufficient to maintain a nip, will be compressed in the land areas 122 reducing the porosity in the land areas.

Figure 16:
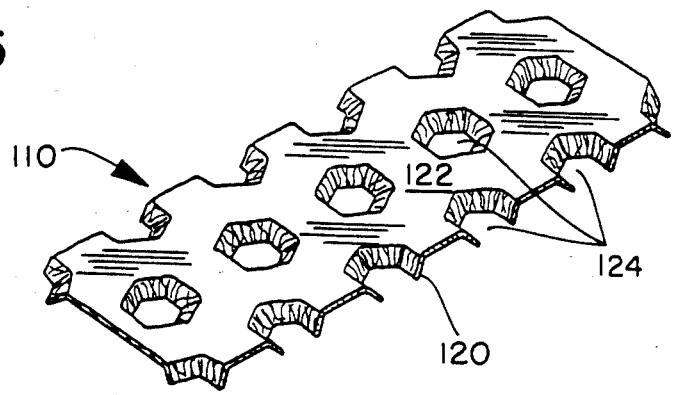

FIG. 16 illustrates in greater detail a web modified by the calendering method of FIG. 15. In this case the projections between land areas 122 include apertures 124.

Figure 17:
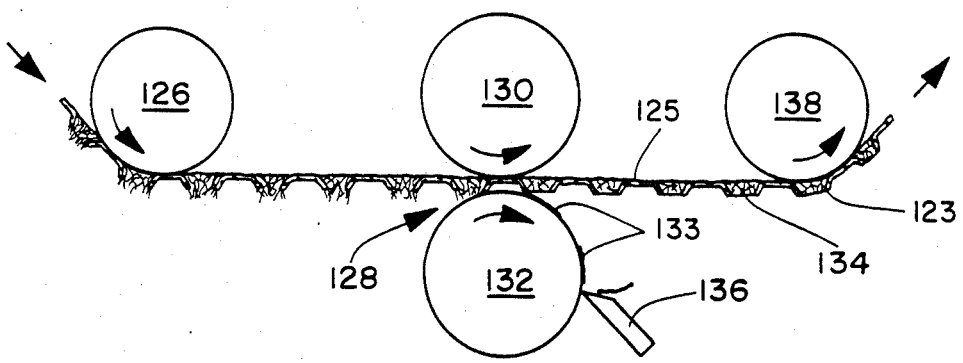
FIG. 17 illustrates an aperturing means in accordance with one aspect of the present invention, and FIG. 18 the resulting web in schematic form.

FIG. 17 illustrates one of the alternative aperturing steps using heat. As shown, the projections 123 extend downward from web 125 which is directed over guide roll 126 to nip 128 which is a fixed gap between rolls 130, 132. These rolls are rotated, and bottom roll 132 is heated to a temperature above the melting point of the polymer used to form the web 125. In a preferred embodiment roll 130 may be chilled to reduce stiffening of the sheet. The fibers covering the projections adhere to roll 132 and are drawn away forming apertures 134. Polymer 133 adhering to the roll is removed by blade 136, and the web is removed by guide roll 138.

Figure 18:
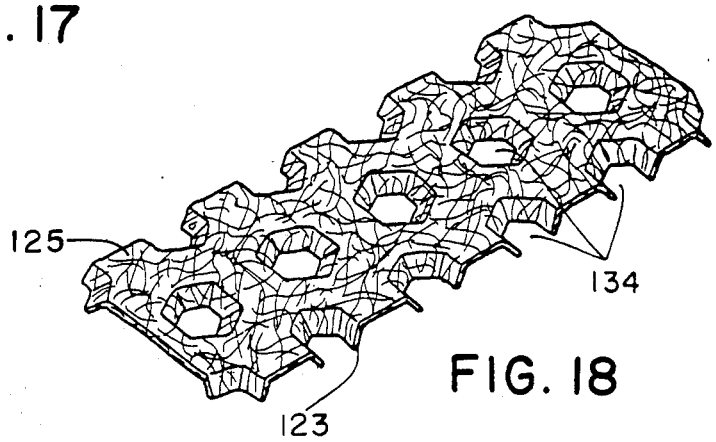

FIG. 18 is an illustration of web 125 formed in accordance with FIG. 17.

Figure 19:
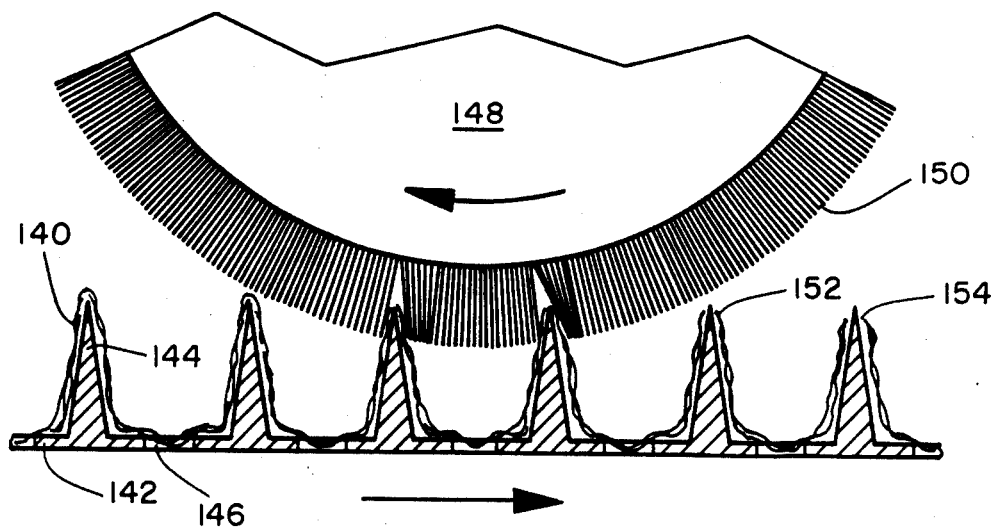
FIGS. 19 and 20 illustrate alternative aperturing means in accordance with the present invention.

FIG. 19 schematically illustrates means for forming webs with apertured projections starting with a process such as is illustrated in FIG. 1. In general, web 140 on carrier 142 having pins 144 and openings 146 for vaccum assist is contacted by brush roll 148 having an exterior surface covered with bristles 150. The bristles extend part way into areas between the pins 144 pushing fibers 152 away from the tops of pins 144 thus producing apertures 154.

Figure 20:
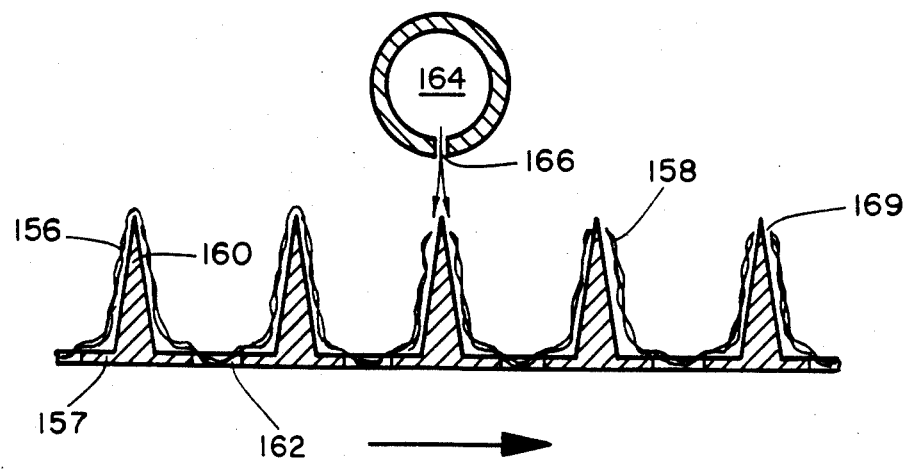

FIG. 20 similarly illustrates an alternative projection perforating means. In this case web 156 is supported on carrier 157 having pins 160 and openings 162 but passes under air duct 164 having slit 166 which directs air against the web 156 forcing filaments 158 away from the tops of the pins producing apertures 169.

Figure 21:
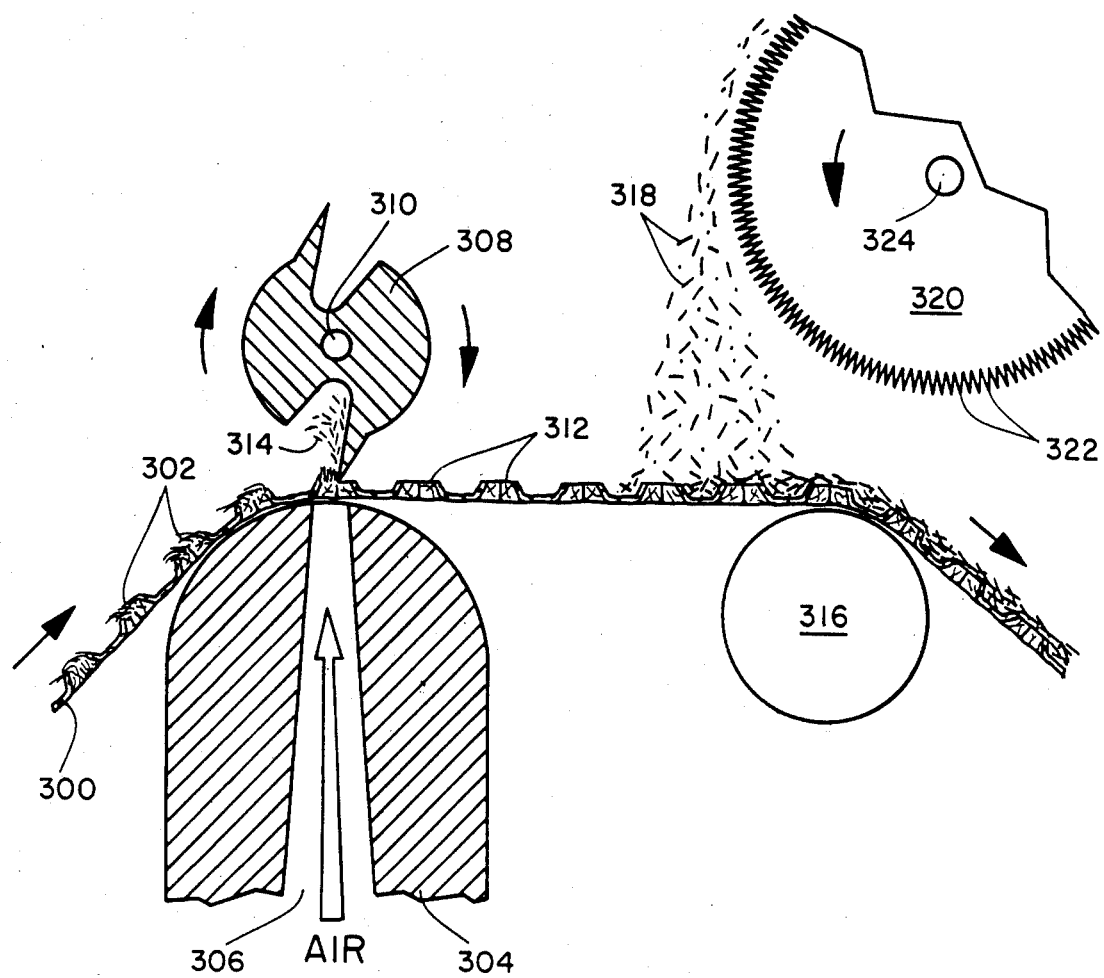
FIG. 21 illustrates an alternative aperturing means.
Figure 22:
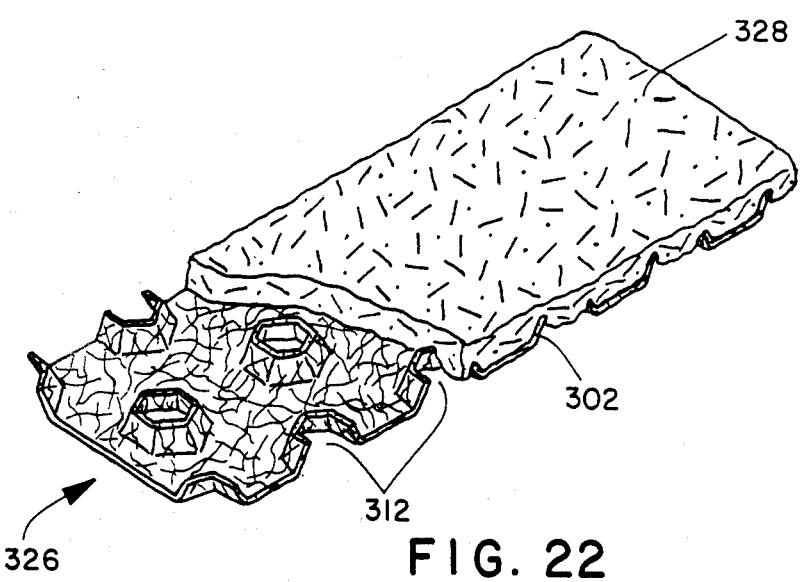
FIG. 22 illustrates a resulting apertured web.

FIG. 21 illustrates an alternative aperturing step adapted for use with webs formed as in either FIG. 1 or FIG. 5. In this case web 300 having projections 302 moves in the direction indicated over anvil 304 having air slot 306. Blade 308 rotates about pivot 310 shaving the tops of projections 302 producing apertures 312. The air flow through slot 306 which aligns fibers 314 which facilitates removal. The shaved web may be drawn over support roll 316 for storage or further processing. In a further preferred embodiment additional fibers 318 which may be of an absorbent material such as wood pulp are deposited on the side of web 300 with projections 302. The fibers may be added by means of picker roll 320 having teeth 322 rotating about pivot 324. FIG. 22 schematically illustrates a shaved web 326 resulting from the step of FIG. 21 with a wood pulp layer 328 added.

Figure 23:
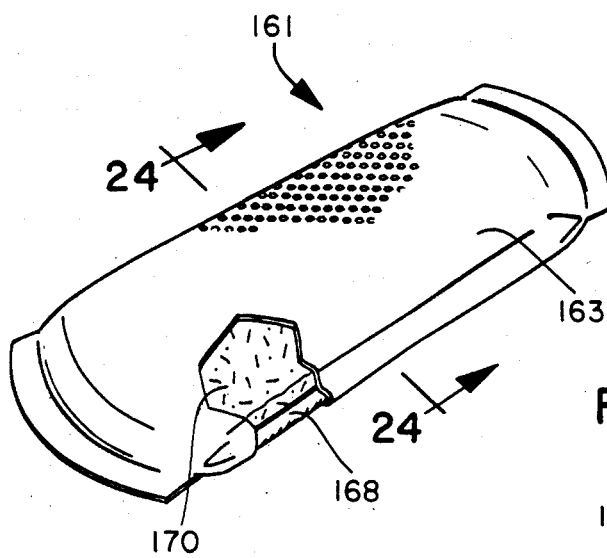
FIG. 23 illustrates a sanitary napkin product formed in accordance with the present invention.

FIG. 23 schematically illustrates a conventional type of sanitary napkin 161 partially broken away to show cover of the invention 163, absorbent 170 and baffle 168.

Figure 24:
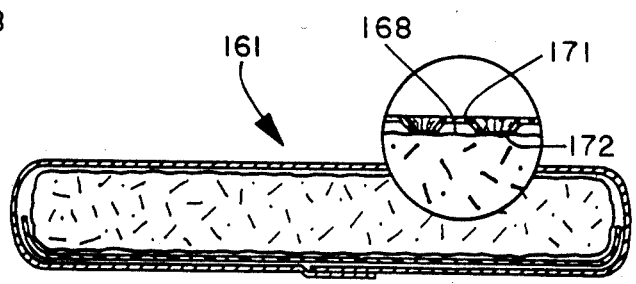
FIG. 24 is a cross-section of the product of FIG. 23 taken along lines 24—24.

FIG. 24 shows the sanitary napkin 161 of FIG. 23 in cross-section taken along lines 24—24 of FIG. 23. As shown, projections 172 contact absorbent 168 and permit flow through to the absorbent while limiting contact in land areas 171 providing separation and inhibiting flow back.

Figure 25:
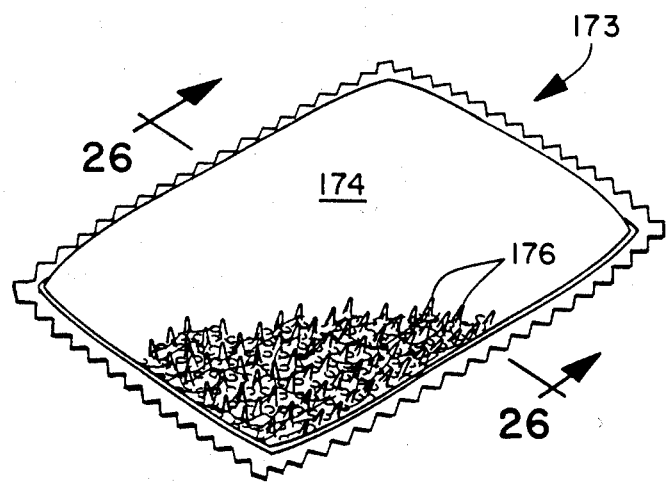
FIG. 25 is a scrubbing device formed in accordance with the present invention, shown in schematic form.

FIG. 25 illustrates a scrubbing device formed from a higher basis weight material of the present invention. As shown scrubber 173 comprises a pad with outer surface of web 174 with hollow projections 176 extending outwardly. In this case, the projections 176 are not apertured.

Figure 26:
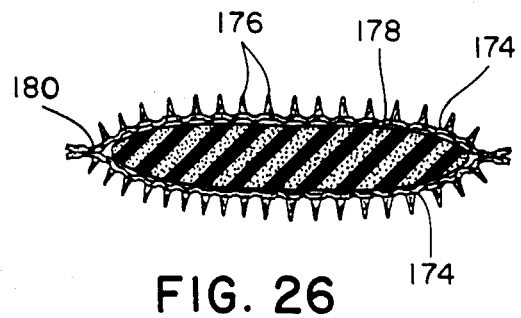
FIG. 26 is a cross-section of the pad of FIG. 25 taken along lines 26—26.

FIG. 26 shows the scrubber of FIG. 25 in cross-section taken along lines 26—26 of FIG. 25 illustrating sponge central pad 178 which may be, for example, polyurethane and of desired hardness for the intended use. For convenience, cover 174 may be formed of two halves and bonded peripherally along line 180 by heat or adhesive as will be apparent to those skilled in this art.

Figure 27:
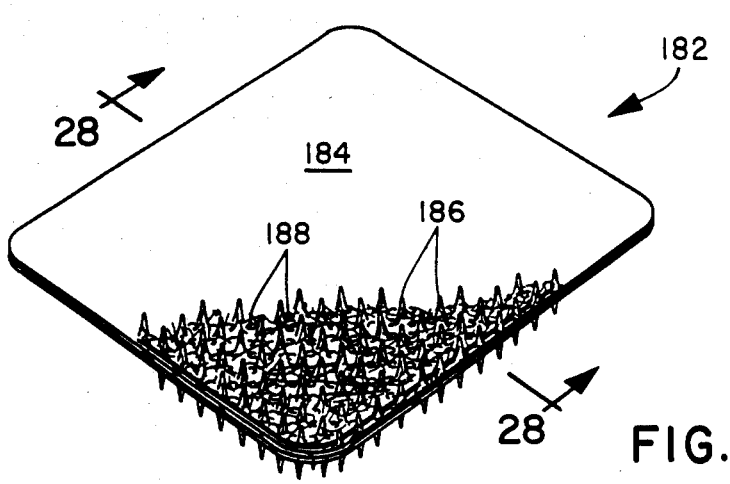
FIG. 27 is a disposable washcloth formed in accordance with the present invention shown in schematic form.

FIG. 27 schematically illustrates a washcloth 182 having a cover 184 including hollow projections 186 and, in the land areas, apertures 188.

Figure 28:
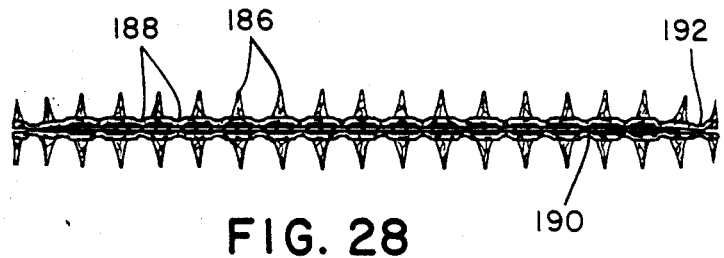
FIG. 28 is a cross-section of the washcloth of FIG. 27 taken along lines 28—28.

FIG. 28 shows the washcloth of FIG. 27 in cross-section taken along lines 28—28 of FIG. 27. The washcloths may be formed in much the same manner as the scrubber of FIG. 25 except that the center pad is thinner and includes an absorbent or strength enhancing layer 190 of tissue, spunbonded nonwoven or meltblown nonwoven, for example. Bonding along peripheral line 192 may be similarly achieved.

Figure 29:
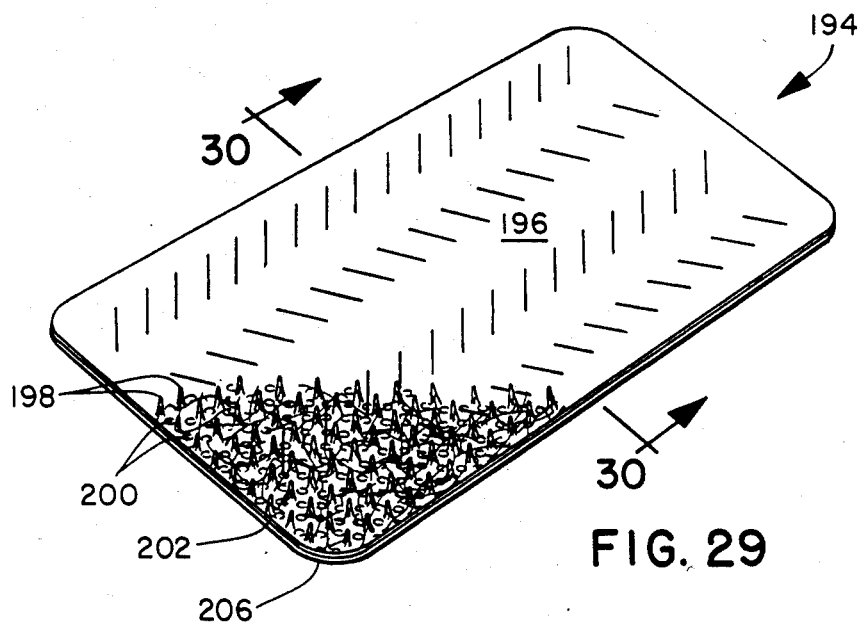
FIG. 29 is an absorbent mat product formed in accordance with the present invention shown in schematic form.
Figure 30:
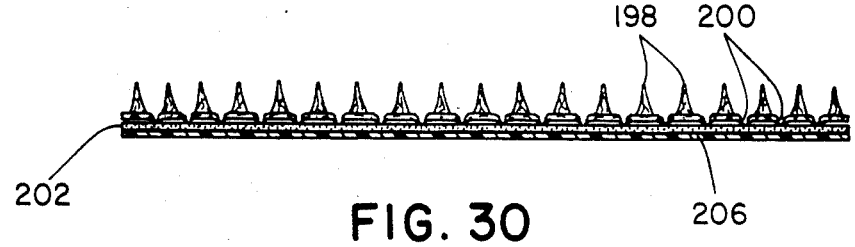
FIG. 30 is a cross-section of the mat of FIG. 29 taken along lines 30—30.

FIG. 29 illustrates schematically a product form of the present invention as a bathmat. Bathmat 194 includes a laminate of walking surface 196 including a nonwoven web of the present invention with outwardly extending hollow projections 198 and apertures 200 in the land areas. Absorbent layer 202 in one embodiment is formed from pulp fluff which, when combined imparts a desired stiffness to the bathmat. As shown in greater detail in FIG. 30 which is a cross-section taken along lines 30—30 of FIG. 29, bottom layer 206 may either be of an impervious material or a rubber-like nonwoven. In any event, the exposed bottom surface has a coefficient of friction sufficient to minimize slipping under conditions of use.

Figure 31:
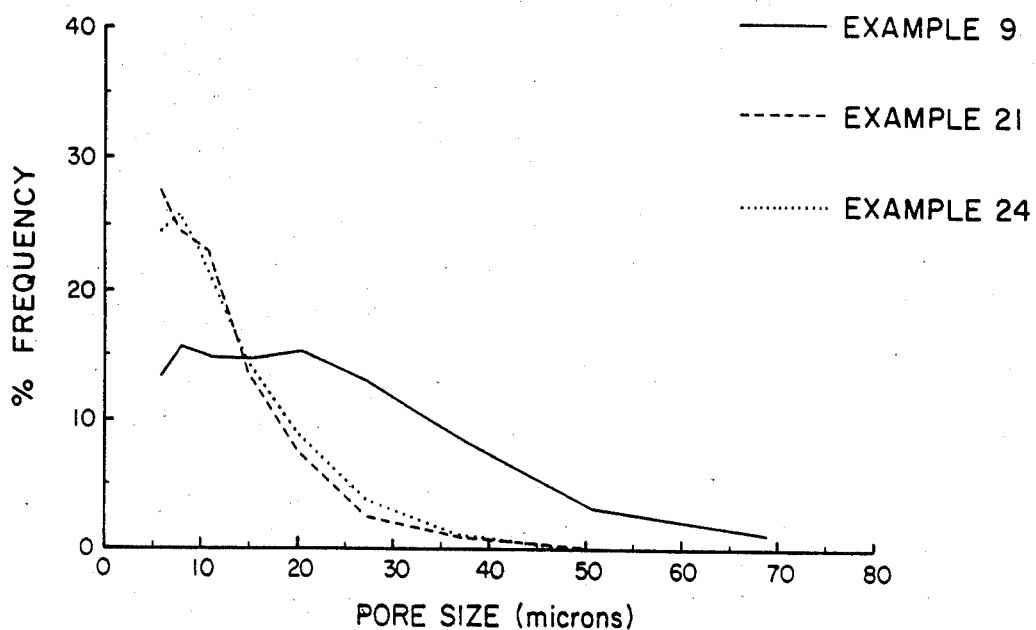
FIG. 31 is a graph showing pore size distribution obtained with certain embodiments of the nonwoven fabrics having apertured projections in accordance with the invention including those formed with a wax component and modified by calendering.

FIG. 31 is a graph showing pore size distribution versus frequency percent occurrence. The solid line represents an untreated web, Example 9. The dotted line indicates a material of the invention, Example 24, calendered and without wax. The dashed line indicates the material of Example 21 including wax. As shown, the use of either wax or calendering greatly increases the frequency of smaller pores thus enhancing the hiding power of the web, particularly for applications as a liner for a sanitary napkin. The smaller pore retard entrapment of, for example, menstrual fluid resulting in a cleaner, dryer cover material.

Figure 32:
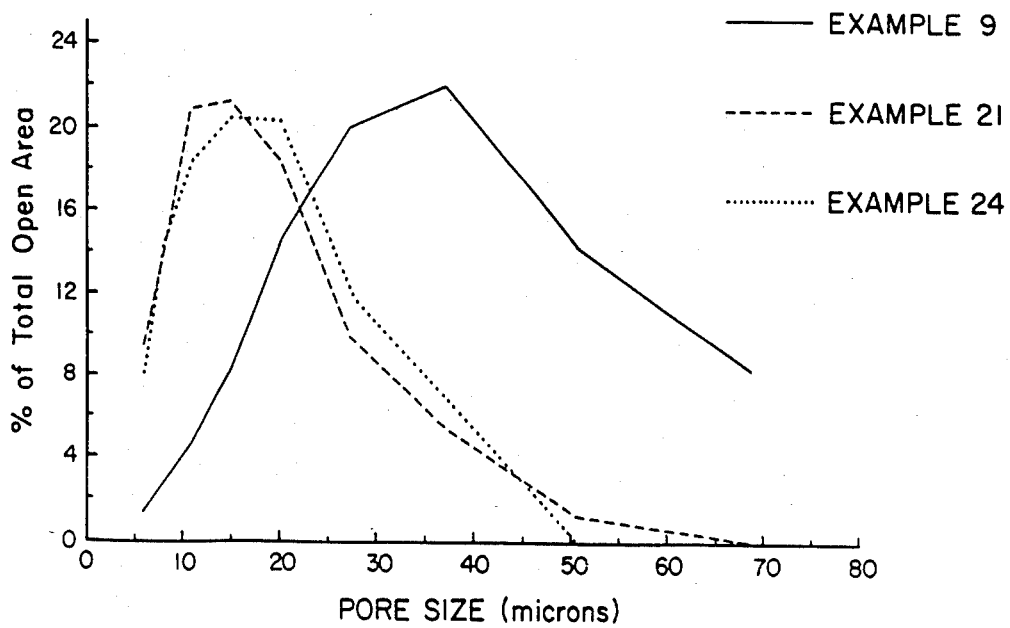
FIG. 32 is a graph showing percent of total open area of the fabrics tested for FIG. 31.

FIG. 32 is a similar graph with the same materials represented in the same manner except that pore size is shown as a function of percent total open area. Again, the greater concentration of the desirable smaller pores is demonstrated.

As will be apparent to those skilled in this art, the present invention is susceptible of many product forms, and the foregoing are illustrative only of several preferred embodiments.

The invention will now be further illustrated by way of specific examples.

EXAMPLES

Example 1

Using apparatus schematically illustrated in FIG. 1, a web was formed having an array of hollow projections as generally shown in FIG. 9. The polymer used was a linear low density polyethylene identified as DOW XV-61800.06. The die tip had orifices with a diameter of 0.3683 mm, and it was operated at a temperature of 525° F. and pressure of 154 psi. The extruded polymer was contracted on both sides by primary air at a temperature of 550° F., pressure of 1 psi and rate of 55 SCFM. The result was a throughput of 2.4 lb/in-hr which was collected at a distance of 9 inches. The forming surface was as shown in FIG. 2 with 15 projections per cm², each projection cone-shaped with a base diameter of 1.5 mm and height of 6.25 mm. The forming surface was driven at a rate to produce a basis weight of 30.33 gsm for the web.

Example 2

Example 1 was repeated except that the forming surface was driven at a rate to produce a basis weight of 101.1 gsm.

Example 3

Example 2 was repeated except that a conventional meltblowing process was used without forming surface with projections for form a web having a basis weight of 30.31 gsm.

Example 4

Example 1 was repeated using polypropylene identified as Exxon 3145. In this case the die tip was operated at a temperature of 453° F. and pressure of 104 psi. The primary air temperature was changed to 400° F. and rate to 60 SCFM and the resulting basis weight was 30.33 gsm. Example 5

Example 4 was repeated driving the forming surface at a rate to produce a web of a basis weight of 101.1 gsm.

Example 6

Example 5 was repeated using standard meltblowing as in Example 3.

Example 7

The operating conditions of the equipment of the previous examples were modified to produce a web from polyurethane identified as Estane 58887 at a throughput of 2.4 lb/in-hr for a basis weight of 250 gsm.

Example 8

Using the process schematically illustrated in FIG. 5 a web was formed having an array of open, hollow projections generally as illustrated in FIG. 12. The forming surface had a configuration as in FIG. 6 to produce a web with a projection density of about 53 projections per square centimeter with opening average diameter of about 526 microns. The polymer used was polyethylene (Dow XV 61800.06 from Dow Chemical) which was extruded at a melt temperature of 329° C., air temperature of 274° C., air flow of 140 SCFM, and collected at a forming distance of 7.6 cm. The collecting surface was moved at a rate to provide a web basis weight of 59 grams per square meter.

Example 9

Example 8 was repeated except that the forming surface pattern was changed to that producing a web with a hole size of 721 microns, 39 open, hollow projections per square centimeter, and the web had a basis weight of 66 grams per square meter.

Example 10

Example 8 was repeated except that the forming surface pattern was changed to that producing a web having about 26 open, hollow projections per square centimeter with an average diameter of about 855 microns.

Example 11

Example 8 was repeated except that the forming surface pattern and operating conditions were changed to produce a 58 grams per square meter basis weight web having about 20 open, hollow projections per square centimeter with an average diameter of about 1171 microns.

Example 12

Example 8 was repeated except that the forming surface pattern was as in FIG. 7 and operating conditions were changed to produce a 54 grams per square meter basis weight web having about 40 open, hollow projections per square centimeter with an average diameter of about 686 microns.

Example 13

Example 12 was repeated except that the forming surface pattern and operating conditions were changed to produce an 84 grams per square meter basis weight web having about 22 open, hollow projections per square centimeter with an average diameter of about 1155 microns.

Example 14

Example 8 was repeated except that the forming surface pattern was as in FIG. 8 and the operating conditions were changed to produce a 54 grams per square meter basis weight web having open, hollow projections with an average hole breadth 450 microns and percent open area of 5.3.

Example 15

Example 9 was repeated with polypropylene (designated as 3145 from Exxon) and the forming conditions were as follows: Melt temperature of 307° C., air temperature of 232° C., air flow of 100 SCFM, forming distance of 7.6 cm and adjusted to produce a basis weight of 16 grams per square meter and average hole size of about 721 microns.

Example 16

Example 15 was repeated except at a basis weight of 33 grams per square meter.

Example 17

Example 15 was repeated except at a basis weight of 37 grams per square meter.

Example 18

Example 9 was repeated except at a basis weight of 25 grams per square meter and a melt temperature of 316° C.

Example 19

Example 18 was repeated except that 1 percent by weight hydrocarbon processing aid (identified as Ross Wax 165, a paraffin wax) was added to the polymer, and the resulting basis weight was 23 grams per square meter.

Example 20

Example 19 was repeated except that the amount of hydrocarbon processing aid was raised to 5 percent by weight and the resulting basis weight was 22 grams per square meter.

Example 21

Example 19 was repeated except that the amount of hydrocarbon processing aid was raised to 10 percent by weight, and the resulting basis weight was 19 grams per square meter.

Example 22

Example 19 was repeated except that the amount of hydrocarbon processing aid was raised to 20 percent by weight, and the resulting basis weight was 23 grams per square meter.

Example 23

This example was 28 grams per square meter basis weight conventional meltblown polyethylene produced generally as described in U.S. Pat. No. 3,978,185 to Buntin et al dated Aug. 31, 1976 under the following conditions: melt temperature 332° C., air temperature 274° C., air flow 120 SCFM, forming distance 19 cm.

Example 24

The web of Example 9 was calendered on both sides of the web as shown in FIG. 15. The calendered web had an average hole size (breadth) of 870 microns with a percent open area of 22.

Example 25

The web of Example 10 was calendered as in Example 24 with a resulting average hole size (breadth) of 961 microns and average percent open area of 18.3.

Example 26

The web of Example 11 was calendered as in Example 24 with a resulting average hole size (breadth) of 1267 microns and average percent open area of 25.9.

Example 27

The web of Example 9 was calendered as in FIG. 15 and received a fiber layer added by fiber addition means as shown in FIG. 21. The fiber added was pulp CR54 available from Kimberly-Clark Corporation added at about 30 gsm additional fiber.

Example 28

The web of Example 10 was treated as in Example 27.

Example 29

Process of FIG. 5 was to form a web on a surface having 0.075 in. diameter staggered circles, 0.1 inch centers with 115 holes per square inch and 51 percent open area using a melt temperature of 316° C., air temperature of 260° C., air flow of 145 SCFM, and forming distance of 9 cm for basis weight of 16.6 gsm.

The materials of Examples 1 through 23 were tested in accordance with the present invention to determine grab tensile, elongation, energy to rupture, trap tear, bulk, Frazier porosity, and drape properties. The results of these tests are set forth in the following Table.

TABLE I

| EXAMPLE | GRAB TENSILE MD (lb) | GRAB TENSILE CD (lb) | ELONGATION MD (%) | ELONGATION CD (%) | ENERGY TO RUPTURE MD (in/lb) | ENERGY TO RUPTURE CD (in/lb) | TRAP TEAR MD (lb) | TRAP TEAR CD (lb) | PEAK HEIGHT (cm) | FRAZIER POROSITY (cfm) | DRAPE/STIFFNESS MD (cms) | DRAPE/STIFFNESS CD (cms) | BULK DENSITY (g/cc) |
|---|---|---|---|---|---|---|---|---|---|---|---|---|---|
| 1 | 0.9 | 0.9 | 59 | 81 | 2.0 | 2.2 | N/A | N/A | 0.43 | 1220 | 1.57 | 1.80 | 0.007 |
| 2 | 3.9 | 4.2 | 65 | 63 | 8.0 | 7.3 | 1.62 | 1.73 | 0.41 | 485 | 3.57 | 3.225 | 0.024 |
| 3 | 5.9 | 5.0 | 50 | 36 | 9.6 | 7.5 | 2.18 | 2.56 | 0.08 | N/A | 4.05 | 2.80 | 0.04 |
| 4 | 3.7 | 2.1 | 50 | 50 | 4.5 | 2.1 | 1.05 | 2.50 | 0.38 | 1240 | 2.30 | 3.175 | 0.007 |
| 5 | 5.4 | 4.6 | 61 | 54 | 6.7 | 4.8 | 1.41 | 1.51 | 0.61 | 540 | 4.55 | 4.35 | 0.016 |
| 6 | 11.2 | 12.8 | 5 | 45 | 2.4 | 14.9 | 3.98 | .78 | 0.08 | 168 | 6.0 | 4.85 | 0.024 |
| 7 | | | | | | | 7.16 | N/A | 0.36 | 520 | 2.65 | N/A | 0.007 |
| 8 | 3.5 | 3.7 | 24 | 42 | 1.6 | 2.4 | 0.59 | 0.37 | 0.104 | 375 | 2.5 | 2.2 | 0.057 |
| 9 | 4.2 | 2.4 | 24 | 20 | 2.0 | 1.0 | 0.68 | 0.58 | 0.094 | 496 | 3.6 | 2.6 | 0.070 |
| 10 | 3.8 | 3.4 | 20 | 12 | 1.5 | 0.8 | 0.50 | 0.21 | 0.076 | 469 | 2.4 | 2.8 | 0.077 |
| 11 | 3.2 | 2.6 | 25 | 19 | 1.6 | 0.9 | 0.48 | 0.33 | 0.079 | 606 | 2.8 | 2.9 | 0.074 |
| 12 | 2.0 | 2.3 | 32 | 28 | 1.1 | 1.2 | 0.58 | 0.34 | 0.165 | 599 | 2.5 | 3.2 | 0.032 |
| 13 | 2.0 | 2.0 | 13 | 21 | 0.5 | 0.8 | 0.39 | 0.52 | 0.183 | 880 | 3.4 | 4.6 | 0.046 |
| 14 | 1.2 | 2.0 | 49 | 20 | 0.9 | 0.7 | 0.30 | 0.50 | 0.241 | 856 | 1.6 | 4.7 | 0.022 |
| 15 | 0.9 | 1.3 | 48 | 53 | 0.8 | 1.4 | 0.14 | 0.19 | 0.053 | 824 | N/A | N/A | 0.031 |
| 16 | 3.1 | 2.7 | 47 | 48 | 3.1 | 2.5 | 0.39 | 0.22 | 0.112 | 341 | N/A | N/A | 0.029 |

TABLE I-continued

| EXAMPLE | GRAB TENSILE MD (lb) | GRAB TENSILE CD (lb) | ELONGATION MD (%) | ELONGATION CD (%) | ENERGY TO RUPTURE MD (in/lb) | ENERGY TO RUPTURE CD (in/lb) | TRAP TEAR MD (lb) | TRAP TEAR CD (lb) | PEAK HEIGHT (cm) | FRAZIER POROSITY (cfm) | DRAPE/STIFFNESS MD (cms) | DRAPE/STIFFNESS CD (cms) | BULK DENSITY (g/cc) |
|---|---|---|---|---|---|---|---|---|---|---|---|---|---|
| 17 | 3.7 | 2.7 | 45 | 20 | 3.5 | 1.2 | 0.39 | 0.23 | 0.119 | 401 | N/A | N/A | 0.031 |
| 18 | 1.5 | 1.1 | 95 | 91 | 3.3 | 2.1 | 0.60 | 0.33 | 0.097 | N/A | N/A | N/A | 0.026 |
| 19 | 1.3 | 1.0 | 103 | 77 | 3.0 | 1.5 | 0.60 | 0.27 | 0.081 | N/A | N/A | N/A | 0.028 |
| 20 | 1.1 | 0.9 | 68 | 100 | 2.2 | 2.0 | 0.60 | 0.32 | 0.081 | N/A | N/A | N/A | 0.027 |
| 21 | 1.0 | 0.7 | 79 | 85 | 2.1 | 1.4 | 0.37 | 0.21 | 0.071 | N/A | N/A | N/A | 0.027 |
| 22 | 1.0 | 0.7 | 49 | 46 | 1.4 | 0.7 | 0.26 | 0.12 | 0.074 | N/A | N/A | N/A | 0.031 |
| 23 | 0.7 | 1.4 | 42 | 37 | 1.0 | 1.1 | 0.30 | 0.17 | 0.053 | 772 | N/A | N/A | 0.053 |
| (Control) 29 | 0.7 | 0.5 | 105 | 103 | 1.2 | 1.2 | 0.35 | 0.18 | 0.043 | 1082 | N/A | N/A | 0.015 |

The materials of Examples 9-12 were tested along with apertured film from commercially available sanitary product (Always brand) (designated "APA"), apertured film on a commercially available sanitary product (Silhouette brand) (designated "APB"), polypropylene spunbonded fabric 13 gsm, (designated "SB") and bonded carded web, (designated "BCW") for surface moisture and blotter rewet. Surface moisture results were obtained by a test which uses a conductivity probe to determine surface moisture of a material as a function of time elapsed from fluid application. The fluid included droplets of oil encapsulated in gelatin and had a surface tension of 55 dynes/cm. Three cubic centimeters were added to the sample covering a type 59E conductivity probe from Delmhorst Instrument Co. A conductivity reading was taken at the indicated time intervals and, using standard decay curve for conversion factors, was recorded as % moisture content. Blotter rewet results were obtained by measuring the amount of 8 cubic centimeters of a composition (as described in U.S. Pat. No. 4,397,644 to Matthews et al dated Aug. 9, 1983 in col. 7, lines 12+, incorporated herein by reference, except that no surfactant was added) transferred from the sample to a standard Veri-Good 120 lb. basis weight blotter material from James River under conditions of 0.25 PSI for 3 minutes, 0.5 PSI pressure for 3 minutes, and a final 3 minutes at 1 PSI. Table II gives the results demonstrating that drier covers may be obtained in accordance with invention.

TABLE II

| Example | Surface Moisture (%) 10 sec. | Surface Moisture (%) 80 sec. | Surface Moisture (%) 300 sec. | Blotter Rewet (After 1 p.s.i.) |
|---|---|---|---|---|
| Ex. 9 | 60 | 60 | 63 | 0.13 |
| Ex. 10 | 57 | 38 | 39 | 0.13 |
| Ex. 11 | 54 | 56 | 65 | 0.17 |
| Ex. 12 | 55 | 53 | 42 | 0.1 |
| APA | 69 | 68 | 73 | 0.03 |
| APB | 89 | 91 | 93 | 0.97 |
| SB | 82 | 85 | 88 | 0.79 |
| BCW | 63 | 65 | 71 | 0.49 |

The materials of Examples 29 were tested for fiber orientation in the land and projection areas by the test method described above.

The results are shown in Table III.

TABLE III

| Example | Land Area Orientation (°) | Projection Area (°) |
|---|---|---|
| 1 | 47 | 72 |
| 2 | 47 | 64 |
| 29 | 61 | 72 |

The effect of fluff addition as in FIG. 21 was demonstrated by testing the materials of Examples 9, 10, 27 and 28 for absorbency rate as in the above described U.S. Pat. No. 4,397,644 to Matthews et al dated Aug. 9, 1983 using the composition without surfactant and 8 ccs added. In this case the time for 6 ccs to be absorbed was recorded. The test results were 120 seconds, 23 seconds, 14.5 seconds, and 11.8 seconds for the respective examples demonstrating the rapid rate improvement obtained with the added fluff layer.

As the data above indicate, webs of the present invention provide improved properties and are extremely versatile since they may be produced in widely varying forms. In this manner the webs of the present invention having projections as described provide highly useful materials for components of personal care product and for a wide variety of other uses as well.

Thus it is apparent that there has been provided in accordance with the invention an improved nonwoven web with projections and method of making that fully satisfy the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. Nonwoven fabric comprised of overlapping thermoplastic fibers or filaments defining an array of hollow projections extending out of said fabric and separated by planar land areas in a plane taken along a line parallel to said fabric ignoring the projections and said fabric characterized by at least a 5 degree higher average degree of fiber or filament alignment in the projections than in the land areas.

2. Nonwoven fabric of claim 1 wherein the fibers or filaments are selected from the group consisting of polyolefins, polyesters, polyamides and mixtures and blends thereof.

3. Nonwoven fabric of claim 2 wherein the theremoplastic is selected from the group consisting of polypropylene, polyethylene and mixtures and blends thereof.

4. Nonwoven fabric of claims 1, 2, or 3 wherein the projections have a height of about 0.3 to about 25 millimeters and the array consists of about 1 to about 80 projections per square centimeter.

5. Nonwoven fabric of claims 1, 2, or 3 wherein the projections have a height of about 0.5 to about 10 millimeters and the array consists of about 5 to about 50 projections per square centimeter.

6. Nonwoven fabric of claim 4 having a bulk density in the range of from about 0.001 to about 0.11 grams per cubic centimeter.

7. Nonwoven fabric of claim 5 having a bulk density in the range of from about 0.001 to about 0.11 grams per cubic centimeter.

8. Nonwoven fabric of claim 6 having a basis weight in the range of from about 20 to 300 grams per square meter.

9. Nonwoven fabric of claim 7 having a basis weight in the range of from about 20 to 300 grams per square meter.

10. Nonwoven fabric of claim 6 having a basis weight in the range of from about 20 to 70 grams per square meter.

11. Nonwoven fabric of claim 7 having a basis weight in the range of from about 20 to 70 grams per square meter.

12. Nonwoven fabric of claim 8 having a volume ratio of projections to volume between projections in the range of from about 1 to 250.

13. Nonwoven fabric of claim 9 having a volume ratio of projections to volume between projections in the range of from about 1 to 250.

14. Nonwoven fabric of claim 4 wherein the projections are apertured.

15. Nonwoven fabric of claim 5 wherein the projections are apertured.

16. Nonwoven fabric of claim 6 wherein the projections are apertured.

17. Nonwoven fabric of claim 7 wherein the projections are apertured.

18. Nonwoven fabric of claim 8 wherein the projections are apertured.

19. Nonwoven fabric of claim 9 wherein the projections are apertured.

20. Nonwoven fabric of claim 10 wherein the projections are apertured.

21. Nonwoven fabric of claim 11 wherein the projections are apertured.

22. Nonwoven fabric of claim 12 wherein the projections are apertured.

23. Nonwoven fabric of claim 13 wherein the projections are apertured.

24. Nonwoven fabric of claim 4 wherein the projections are cone-shaped.

25. Nonwoven web of claim 5 wherein the projections are cone-shaped.

26. Nonwoven web of claim 14 wherein the projections are cone-shaped by extension.

27. Nonwoven web of claim 15 wherein the projections are cone-shaped by extension.

28. Nonwoven web of claim 4 combined with a layer of absorbent fibers deposited onto and covering said projections.

29. Nonwoven web of claim 5 combined with a layer of absorbent fibers deposited onto and covering said projections.

30. Nonwoven web of claim 14 combined with a layer of absorbent fibers deposited onto and covering said projections.

31. Nonwoven web of claim 15 combined with a layer of absorbent fibers deposited onto and covering said projections.

32. Nonwoven web of claim 4 wherein the ratio of the average hollow core volume to the average total projection volume is in the range of from about 0.25 to 0.75.

33. Nonwoven web of claim 5 wherein the ratio of the average hollow core volume to the average total projection volume is in the range of from about 0.25 to 0.75.

34. Nonwoven web of claim 14 wherein the ratio of the average hollow core volume to the average total projection volume is in the range of from about 0.25 to 0.75.

35. Nonwoven web of claim 15 wherein the ratio of the average hollow core volume to the average total projection volume is in the range of from about 0.25 to 0.75.

36. Nonwoven web of claim 4 wherein the land areas are densified.

37. Nonwoven web of claim 5 wherein the land areas are densified.

38. Nonwoven web of claim 14 wherein the land areas are densified.

39. Nonwoven web of claim 15 wherein the land areas are densified.

40. Nonwoven web of claim 4 wherein the fibers or filaments are formed from a blend including a hydrocarbon processing aid.

41. Nonwoven web of claim 5 wherein the fibers or filaments are formed from a blend including a hydrocarbon processing air.

42. Nonwoven web of claim 14 wherein the fibers or filaments are formed from a blend including a hydrocarbon processing aid.

43. Nonwoven web of claim 15 wherein the fibers or filaments are formed from a blend including a hydrocarbon processing aid.

44. A person care product comprising an absorbent layer, impervious backing, and liner wherein the liner comprises the nonwoven web of claim 4 having a basis weight in the range of from about 20 to 70 grams per square meter.

45. A personal care product comprising an absorbent layer, impervious backing, and liner wherein the liner comprises the nonwoven web of claim 5 having a basis weight in the range of from about 20 to 70 grams per square meter.

46. A personal care product comprising an absorbent layer, impervious backing, and liner wherein the liner comprises the nonwoven web of claim 14 having a basis weight in the range of from about 20 to 70 grams per square meter.

47. A personal care product comprising an absorbent layer, impervious backing, and liner wherein the liner comprises the nonwoven web of claim 15 having a basis weight in the range of from about 20 to 70 grams per square meter.

48. A scrubbing device comprising a pad enclosed within an outer surface of the nonwoven web of claim 4.

49. A scrubbing device comprising a pad enclosed within an outer surface of the nonwoven web of claim 5.

50. A scrubbing device comprising a pad enclosed within an outer surface of the nonwoven web of claim 14.

51. A scrubbing device comprising a pad enclosed within an outer surface of the nonwoven web of claim 15.

52. A washcloth comprising the nonwoven web of claim 4 bonded to opposing surfaces of a flexible reinforcing layer.

53. A washcloth comprising the nonwoven web of claim 5 bonded to opposing surfaces of a flexible reinforcing layer.

54. A washcloth comprising the nonwoven web of claim 14 bonded to opposing surfaces of a flexible reinforcing layer.

55. A washcloth comprising the nonwoven web of claim 15 bonded to opposing surfaces of a flexible reinforcing layer.

56. An absorbent mat comprising a walking surface of the nonwoven web of claim 4 bonded to one side of an absorbent layer and an impervious layer on the opposite side of said absorbent layer.

57. An absorbent mat comprising a walking surface of the nonwoven web of claim 5 bonded to one side of an absorbent layer and an impervious layer on the opposite side of said absorbent layer.

58. An absorbent mat comprising a walking surface of the nonwoven web of claim 14 bonded to one side of an absorbent layer and an impervious layer on the opposite side of said absorbent layer.

59. An absorbent mat comprising a walking surface of the nonwoven web of claim 15 bonded to one side of an absorbent layer and an impervious layer on the opposite side of said absorbent layer.

60. Nonwoven web of claim 4 having apertures in said land areas.

61. Nonwoven web of claim 5 having apertures in said land areas.

62. Nonwoven web of claim 14 having apertures in said land areas.

63. Nonwoven web of claim 15 having apertures in said land areas.

64. Method of forming a nonwoven web comprising the steps of,
  (a) depositing thermoplastic fibers or filaments as a web onto a foraminous shaped surface,
  (b) applying a pressure differential to said fibers or filaments while on said surface, to form an array of projections and land areas corresponding to said shaped surface,
  (c) increasing the alignment of said fibers or filaments in the projection areas by at least 5 degrees, and
  (d) separating said web from said surface.

65. Method of claim 64 wherein said pressure differential is applied to projections on said foraminous surface.

66. Method of claim 64 wherein said pressure differential is applied to projection forming apertures in said foraminous surface.

67. Method of claims 64, 65, or 66 including the step of aperturing said projections.

68. Method of claims 64, 65, or 66 including the step of aperturing said land areas.

69. Method of claim 67 including the step of aperturing said land areas.

70. Method of claim 65 including the additional step of densifying said land areas.

71. Method of claims 64, 65, or 66 including the additional step of covering said projections with a layer of absorbent fibers.

* * * * *

UNITED STATES PATENT AND TRADEMARK OFFICE
CERTIFICATE OF CORRECTION

PATENT NO. : 4,741,941

DATED : May 3, 1988

INVENTOR(S) : Stephen M. Englebert, Ann L. Wagner, Gregory S. Hafer
Nanette J. Logsdon It is certified that error appears in the above—identified patent and that said Letters Patent is hereby corrected as shown below:

Column 1, Line 23 "automative" should read --automotive--
Column 1, Line 67 "needing" should read --needling--
Column 2, Line 68 "porjections" should read --projections--
Column 3, Line 9 "denisty" should read --density--
Column 6, Line 4 "characteristics" should read --characteristic--
Column 6, Line 42 "give" should read --given--
Colulmn 7, Line 36 "For for" should read --For--
Column 11, Line 37 "contracted" should read --contacted--
Column 11, Line 56 "for" should read --to--
Column 14, Line 39 "FIG. 5 was to form" should read --FIG. 5 was used to form--
Column 15, Line 42 "with invention" should read --with the invention--
Column 16, Line 55, Claim 3 "theremo-" should read --thermo---
Column 18, Line 24, Claim 41 "air" should read --aid--
Column 18, Line 31, Claim 44 "person" should read --personal--
Column 11, Line 65 "Example 5" should be centered.

Signed and Sealed this

Twenty-first Day of February, 1989

Attest:

DONALD J. QUIGG

Attesting Officer     Commissioner of Patents and Trademarks